(12) United States Patent
Kawamura

(10) Patent No.: US 8,855,754 B2
(45) Date of Patent: Oct. 7, 2014

(54) APPARATUS AND METHOD FOR DETECTING EPILEPSY SEIZURE

(75) Inventor: Tetsuro Kawamura, Ishikawa (JP)

(73) Assignee: Nihon Kohden Corporation, Tokyo (JP)

( * ) Notice: Subject to any disclaimer, the term of this patent is extended or adjusted under 35 U.S.C. 154(b) by 24 days.

(21) Appl. No.: 13/610,845

(22) Filed: Sep. 11, 2012

(65) Prior Publication Data

US 2013/0253353 A1    Sep. 26, 2013

(30) Foreign Application Priority Data

Mar. 23, 2012  (JP) ................................. 2012-067709

(51) Int. Cl.
*A61B 5/0468* (2006.01)
*A61B 5/024* (2006.01)
*A61B 5/00* (2006.01)

(52) U.S. Cl.
CPC ........... *A61B 5/02405* (2013.01); *A61B 5/4035* (2013.01)
USPC ........................................................ 600/509

(58) Field of Classification Search
CPC ............. A61B 5/02405; A61B 5/0245; A61B 5/4035; A61N 1/36064; A61N 1/36053
USPC .................................. 600/508–509, 512, 515
See application file for complete search history.

(56) References Cited

U.S. PATENT DOCUMENTS

| 2008/0319281 A1 | 12/2008 | Aarts |
| 2010/0274303 A1 | 10/2010 | Bukhman |
| 2011/0160603 A1* | 6/2011 | Langston et al. ............. 600/509 |

FOREIGN PATENT DOCUMENTS

| JP | 2009-519803 A | 5/2009 |
| JP | 4416249 B2 | 2/2010 |

\* cited by examiner

*Primary Examiner* — Rex R Holmes
(74) *Attorney, Agent, or Firm* — Kenealy Vaidya LLP

(57) ABSTRACT

An apparatus for detecting an epilepsy seizure, includes: a graph generating unit configured to generate an orthogonal graph where values of heart beat intervals are sequentially plotted while a heart beat interval at an arbitrary timing is set as a first coordinate and a next heart beat interval is set as a second coordinate; and a seizure detecting unit configured to detect the epilepsy seizure based on: a change of a distribution of a group of the plotted values in a first direction perpendicular to a straight line passing an origin and a point where the first and second coordinates are equal to each other; and a change of a distribution of the group of the plotted values in a second direction parallel to the straight line.

13 Claims, 5 Drawing Sheets

LOCUS OF TIME SEQUENCE OF INTERVALS RR IN POINCARÉ PLOTS
UPPER RIGHT IS OBTAINED BEFORE SEIZURE AND LOWER LEFT IS
OBTAINED DURING SEIZURE

APPARATUS AND METHOD FOR DETECTING EPILEPSY SEIZURE

This application claims the priority benefit under 35 U.S.C. §119 of Japanese Patent Application No. 2012-0067709 (filed on Mar. 23, 2012), which is hereby incorporated in its entirety by reference.

BACKGROUND OF THE INVENTION

The present invention relates to an apparatus and method for detecting an epilepsy seizure.

A brain wave is obtained by measuring a change in potential difference caused by a weak electrical activity of the brain by means of scalp electrodes or intracranial electrodes or the like, amplifying a measured signal, and expressing the amplified signal as a waveform. An epilepsy seizure means various signs and symptoms derived from excess discharge of neurons of the cerebral cortex.

An epilepsy seizure is detected as a sudden abnormal wave of a brain wave. Usually, a brain wave obtained by using scalp electrodes is used in the detection. However, a brain wave obtained by this method is susceptible to various kinds of noises. In an epilepsy seizure, a noise which largely affects a brain wave is an electromyogram which is induced with myotonia. An epilepsy seizure often involves a motor seizure and a body motion. Therefore, it often occurs that brain wave signals are covered by an electromyogram and an epilepsy seizure cannot be detected from a brain wave. Furthermore, it is often that an epilepsy seizure localized to the deep brain such as the medial-temporal lobe cannot be detected from a brain wave obtained by using scalp electrodes.

By contrast, a brain wave obtained by using intracranial electrodes is not affected by an electromyogram as compared to a brain wave obtained by using scalp electrodes, and therefore it is possible to record an electrical activity in the deep brain. However, an installation of intracranial electrodes requires a neurosurgical procedure, and hence is highly invasive. Moreover, there is a risk for complications. Therefore, such an installation imposes a heavy burden on the patient.

As a related-art method of detecting an epilepsy seizure without using a brain wave, there is a method in which the heart beat rate is measured by seconds, and an epilepsy seizure is detected by an appearance of a bradycardia following a tachycardia (refer to JP-T-2009-519803).

In the related-art method, an epilepsy seizure is detected based only on a change of the heart beat rate, and therefore there is a possibility that an event which is not an epilepsy seizure may be erroneously detected as an epilepsy seizure. Moreover, there is a further possibility that the sensitivity of detection of an epilepsy seizure cannot be improved.

SUMMARY

This invention provides an apparatus and method for detecting an epilepsy seizure which detects the epilepsy seizure based on a reduction of the heart beat interval and a change of the fluctuation level of the heart beat interval, thereby enabling an epilepsy seizure to be detected without erroneous detection and highly sensitively.

An aspect of the invention provides an apparatus for detecting an epilepsy seizure, the apparatus comprising: a graph generating unit configured to generate an orthogonal graph where values of heart beat intervals are sequentially plotted while a heart beat interval at an arbitrary timing is set as a first coordinate and a next heart beat interval is set as a second coordinate; and a seizure detecting unit configured to detect the epilepsy seizure based on: a change of a distribution of a group of the plotted values in a first direction perpendicular to a straight line passing an origin and a point where the first and second coordinates are equal to each other; and a change of a distribution of the group of the plotted values in a second direction parallel to the straight line.

The seizure detecting unit may detect the epilepsy seizure based on: a change of a standard deviation of the distribution in the first direction; and a change of a standard deviation of the distribution in the second direction.

The seizure detecting unit may detect the epilepsy seizure based on a change of a ratio of the standard deviation of the distribution in the first direction to the standard deviation of the distribution in the second direction.

The seizure detecting unit may detect the epilepsy seizure based on a situation where the ratio is equal to or smaller than a preset threshold.

The threshold may be set for each subject of the heart beat intervals.

The apparatus may further comprise a detection signal outputting unit configured to, when the seizure detecting unit detects the epilepsy seizure, output a detection signal.

The apparatus may further comprise a heart beat interval measuring unit configured to measure the heart beat intervals in continuous heart beats. The graph generating unit may plot the values of the heart beat intervals which are measured by the heart beat interval measuring unit.

The orthogonal graph may be a two-dimensional orthogonal graph, the first coordinate may be a lateral coordinate, and the second coordinate may be a vertical coordinate.

An aspect of the invention provides a method of detecting an epilepsy seizure, the method comprising: generating an orthogonal graph where values of heart beat intervals are sequentially plotted while a heartbeat interval at an arbitrary timing is set as a first coordinate and a next heart beat interval is set as a second coordinate; and detecting the epilepsy seizure based on: a change of a distribution of a group of the plotted values in a first direction perpendicular to a straight line passing an origin and a point where the first and second coordinates are equal to each other; and a change of a distribution of the group of the plotted values in a second direction parallel to the straight line.

The epilepsy seizure may be detected based on: a change of a standard deviation of the distribution in the first direction; and a change of a standard deviation of the distribution in the second direction.

The epilepsy seizure may be detected based on a change of a ratio of the standard deviation of the distribution in the first direction to the standard deviation of the distribution in the second direction.

The epilepsy seizure may be detected based on a situation where the ratio is equal to or smaller than a preset threshold.

The threshold may be set for each subject of the heart beat intervals.

The method may further comprise: outputting a detection signal when the epilepsy seizure is detected.

The method may further comprise: measuring the heart beat intervals in continuous heart beats.

The orthogonal graph may be a two-dimensional orthogonal graph, the first coordinate may be a lateral coordinate, and the second coordinate may be a vertical coordinate.

An aspect of the invention provides a non-transitory computer-readable recording medium in which a computer program causing a computer to execute the method is recorded.

An aspect of the invention provides an apparatus for detecting an epilepsy seizure, the apparatus comprising: a graph generating unit configured to generate an orthogonal graph where values of heart beat intervals are sequentially plotted while a heart beat interval at an arbitrary timing is set as a first coordinate and a next heart beat interval is set as a second coordinate; and a seizure detecting unit configured to detect the epilepsy seizure based on a change of a temporal locus of the plotted values in the graph.

An aspect of the invention provides a method of detecting an epilepsy seizure, the method comprising: generating an orthogonal graph where values of heart beat intervals are sequentially plotted while a heart beat interval at an arbitrary timing is set as a first coordinate and a next heart beat interval is set as a second coordinate; and detecting the epilepsy seizure based on a change of a temporal locus of the plotted values in the graph.

An aspect of the invention provides a non-transitory computer-readable recording medium in which a computer program causing a computer to execute the method according is recorded.

DETAILED DESCRIPTION OF EMBODIMENTS

Hereinafter, an apparatus and program (method) for detecting an epilepsy seizure according to an embodiment of the invention will be described in detail with reference to the drawings.

Figure 1:
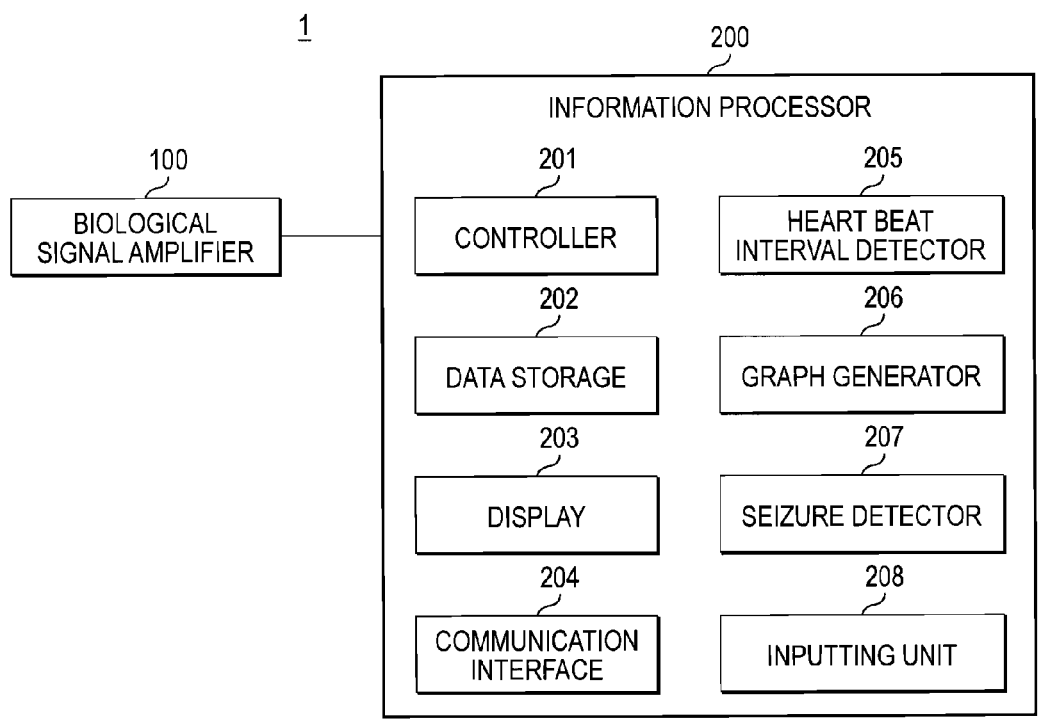
FIG. 1 is a block diagram of an apparatus for detecting an epilepsy seizure according to an embodiment of the invention.

FIG. 1 is a block diagram of the apparatus 1 for detecting an epilepsy seizure according to the embodiment of the invention.

As shown in FIG. 1, the apparatus 1 for detecting an epilepsy seizure according to the embodiment includes a biological signal amplifier 100 and an information processor 200.

The biological signal amplifier 100 is a unit which outputs a temporal variability of the action potential of cardiomyocyte cells due to the heart beat of the subject, in the form of an electrocardiographic signal. The biological signal amplifier 100 may be configured, for example, by: electrodes which are attached to the chest or four limbs of the subject, and which pick up the electrocardiographic signal; an amplifier which amplifies the electrocardiographic signal; a filter which removes noises from the electrocardiographic signal amplified by the amplifier; an A/D converter which digitizes the electrocardiographic signal which is amplified, and from which noises are removed; and an external interface which is used for bidirectionally communicating with an external device.

The information processor 200 includes a controller 201, a data storage 202, a display 203, a communication interface 204, a heartbeat interval detector 205, a graph generator 206, a seizure detector 207, and an inputting unit 208. The information processor 200 may be configured, for example, by a PC (Personal Computer).

The controller 201 controls the components of the information processor 200, and performs various calculation processes in accordance with programs.

The data storage 202 stores electrocardiogram data which are received from the biological signal amplifier 100, various other data, and various programs.

The display 203 can display an electrocardiogram based on the electrocardiogram data which are received from the biological signal amplifier 100. Furthermore, the display 203 can display a graph of Poincaré plots generated by the graph generator 206.

Poincaré plots are plots in which, in continuous heart beats, heart beat intervals are sequentially plotted in a two-dimensional orthogonal graph while the heart beat interval $RR_n$ at an arbitrary timing is set as a lateral coordinate, and the next heartbeat interval $RR_{n+1}$ is set as a vertical coordinate. The heart beat interval RR means the time difference between the peak of the R wave at an arbitrary timing in an electrocardiogram, and that of the next R wave. The suffix n of the heartbeat interval $RR_n$ means the order of the heartbeat interval RR, and the heart beat interval $RR_{n+1}$ indicates the next heart beat interval subsequent to the heart beat interval $RR_n$.

The communication interface 204 receives the electrocardiogram data from the biological signal amplifier 100, and bidirectionally communicates with the biological signal amplifier 100 to mutually transmit and receive various kinds of information.

The heart beat interval detector 205 detects the heart beat interval RR based on the electrocardiogram data received from the biological signal amplifier 100. The heart beat interval RR can be detected by storing the electrocardiogram waveform in the data storage 202, detecting peaks of R waves which are adjacent to each other in the stored electrocardiogram waveform, by calculation, and calculating the interval between the peaks of the R waves.

The graph generator 206 generates a graph of Poincaré plots, based on the heart beat interval RR which is continuously detected for each beat by the heart beat interval detector 205. Namely, the graph generator 206 sequentially plots heart beat intervals in continuous heart beats, in a two-dimensional orthogonal graph while the heart beat interval $RR_n$ at an arbitrary timing is set as a lateral coordinate, and the next heart beat interval $RR_{n+1}$ is set as a vertical coordinate.

The seizure detector 207 detects an epilepsy seizure based on the graph of Poincaré plots generated by the graph generator 206. The method of detecting an epilepsy seizure by the seizure detector 207 will be described later.

When an epilepsy seizure is detected, the seizure detector 207 may output a detection signal through the communication interface 204. In this case, the detection signal can be used as a trigger for initiating means for avoiding a danger associated with an epilepsy seizure.

The inputting unit 208 is a unit to which information for identifying the subject is to be input. The information for identifying the subject which is input through the inputting unit 208 is stored in the data storage 202 while being correlated with the electrocardiogram data of the subject and the graph of Poincaré plots.

Figure 2:
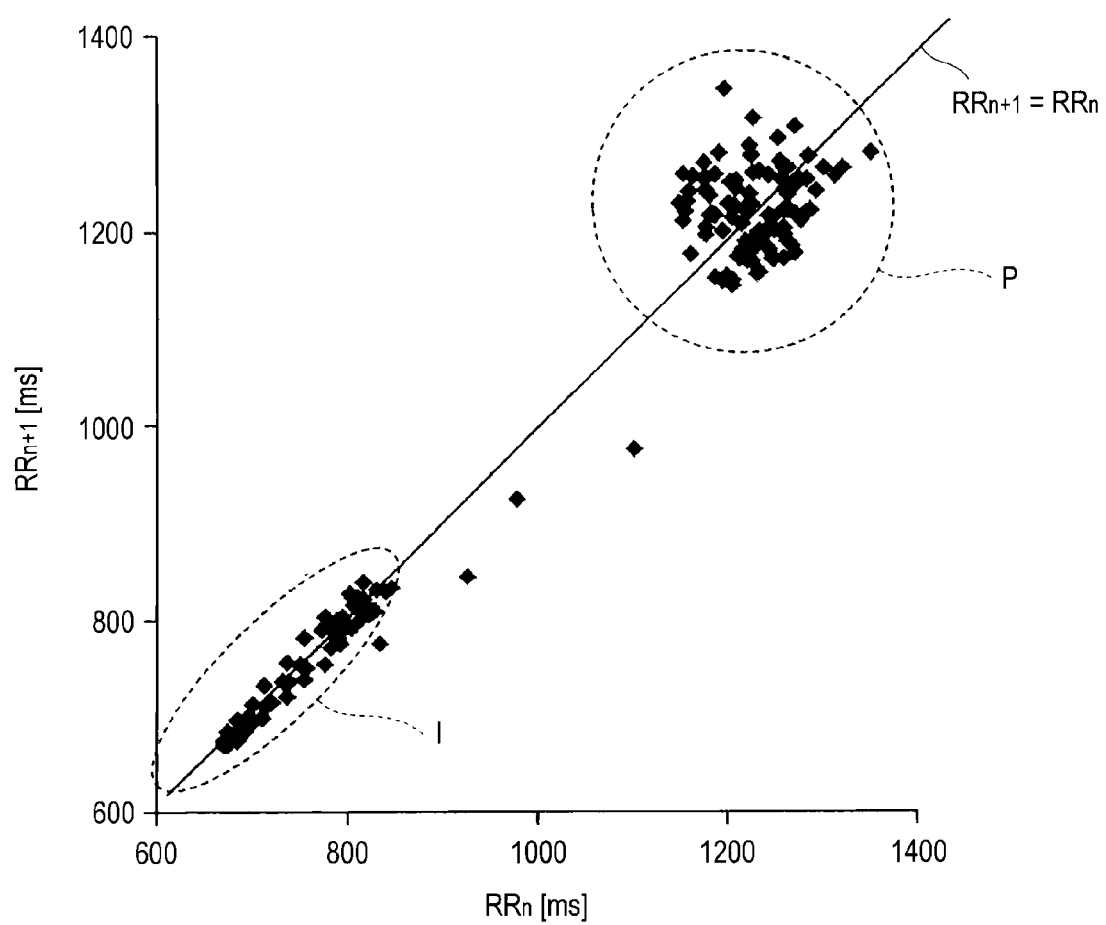
FIG. 2 is a view illustrating a graph in which Poincaré plots are plotted before and after an occurrence of an epilepsy seizure.

FIG. 2 is a view illustrating a graph in which Poincaré plots are generated before and after an occurrence of an epilepsy seizure. In the graph shown in FIG. 2, the abscissa indicates the heart beat interval $RR_n$ which is obtained from the electrocardiogram waveform, and the ordinate indicates the next heart beat interval $RR_{n+1}$ which is obtained from the electrocardiogram waveform, and which is temporally adjacent to the heart beat interval $RR_n$.

The Poincaré plots enclosed by the broken line P in FIG. 2 are Poincaré plots before the occurrence of an epilepsy seizure, and those enclosed by the broken line I are Poincaré plots after the occurrence of the epilepsy seizure.

As seen from the graph of FIG. 2, when an epilepsy seizure occurs, the heart beat interval RR is rapidly shortened, and the fluctuation which is the width of distribution of Poincaré plots in the direction perpendicular to the straight line $RR_{n+1}=RR_n$ is decreased. Namely, when an epilepsy seizure does not occur, Poincaré plots form a loose cluster in the upper right side of the graph of FIG. 2, and, when an epilepsy seizure occurs, rapidly move to the lower left side to converge into the vicinity of the straight line $RR_{n+1}=RR_n$. In FIG. 2, the straight line $RR_{n+1}=RR_n$ is shown in the graph, but the straight line may not be shown in the graph.

In the embodiment, an epilepsy seizure is detected based on two phenomena caused by an occurrence of an epilepsy seizure, i.e., a phenomenon in which the heart beat interval RR is shortened, and that in which the fluctuation of Poincaré plots is decreased. When an epilepsy seizure is detected by using the two characteristic phenomena, an epilepsy seizure can be detected without erroneous detection and highly sensitively.

Figure 3:
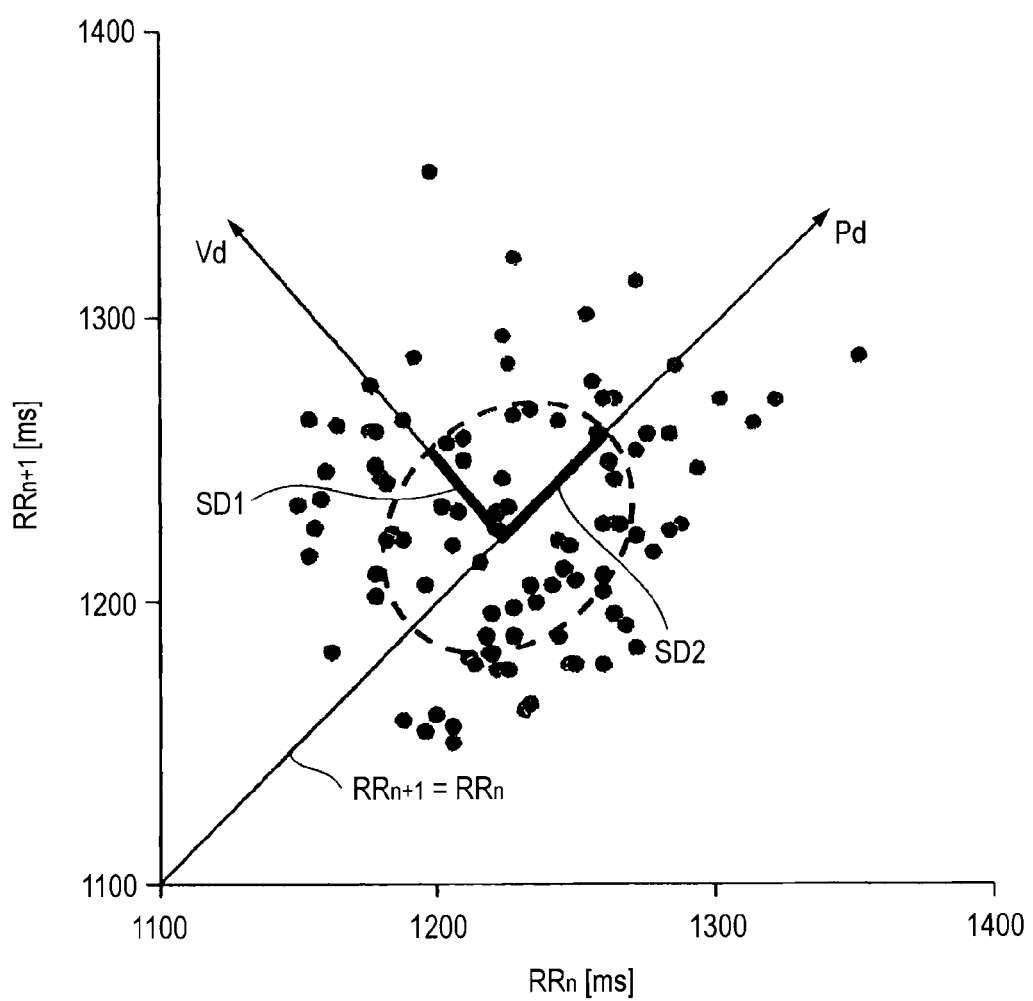
FIG. 3 is a view illustrating parameters which are used in detection of an epilepsy seizure.

FIG. 3 is a view illustrating parameters which are used in detection of an epilepsy seizure by the seizure detector 207. In the graph shown in FIG. 3, similarly with FIG. 2, the abscissa indicates the heart beat interval $RR_n$ which is obtained from the electrocardiogram waveform, and the ordinate indicates the next heart beat interval $RR_{n+1}$ which is obtained from the electrocardiogram waveform, and which is temporally adjacent to the heart beat interval $RR_n$.

The dots shown in FIG. 3 are Poincaré plots, and the straight line $RR_{n+1}=RR_n$ is also shown. The arrow Vd shown in FIG. 3 indicates the direction perpendicular to the straight line $RR_{n+1}=RR_n$, and SD1 which is indicated by the thick line on the arrow Vd indicates the standard deviation of the distribution of Poincaré plots in the direction of the arrow Vd. The arrow Pd shown in FIG. 3 indicates the direction parallel to the straight line $RR_{n+1}=RR_n$, and SD2 which is indicated by the thick line on the arrow Pd indicates the standard deviation of the distribution of Poincaré plots in the direction of the arrow Pd.

The seizure detector 207 detects an epilepsy seizure based on the standard deviation SD1 (hereinafter, referred to simply as "SD1 value") of the distribution of Poincaré plots in the direction Vd perpendicular to the straight line $RR_{n+1}=RR_n$, and the standard deviation SD2 (hereinafter, referred to simply as "SD2 value") of the distribution of Poincaré plots in the direction Pd parallel to the straight line $RR_{n+1}=RR_n$. Specifically, the seizure detector 207 detects an epilepsy seizure based on a change of a value (hereinafter, referred to merely as "SD1/SD2 ratio") which is obtained by dividing the SD1 value by the SD2 value. The seizure detector 207 compares the presently calculated SD1/SD2 ratio with the previously calculated SD1/SD2 ratio, and, if it is determined that there is a significant difference, can detect an epilepsy seizure.

When an epilepsy seizure is detected based on a change of the SD1/SD2 ratio as described above, the rate of erroneous detection of an epilepsy seizure can be further lowered, and the detection sensitivity can be more improved.

Preferably, a threshold for detecting an epilepsy seizure from a change of the SD1/SD2 ratio is set for each subject. This can further improve the sensitivity of detection of an epilepsy seizure.

An adequate weight may be applied to the SD1 value and SD2 value which provide the SD1/SD2 ratio.

Alternatively, the seizure detector 207 detects an epilepsy seizure based on a situation where the SD1 value is equal to or smaller than a preset threshold, and the SD2 value is equal to or larger than a preset threshold. Namely, individual thresholds may be set for the SD1 value and the SD2 value, respectively, and, when the both values exceed the thresholds, an epilepsy seizure may be detected.

Alternatively, an epilepsy seizure may be detected based on a change of a value which is obtained by dividing the SD2 value by the SD1 value.

Figure 4:
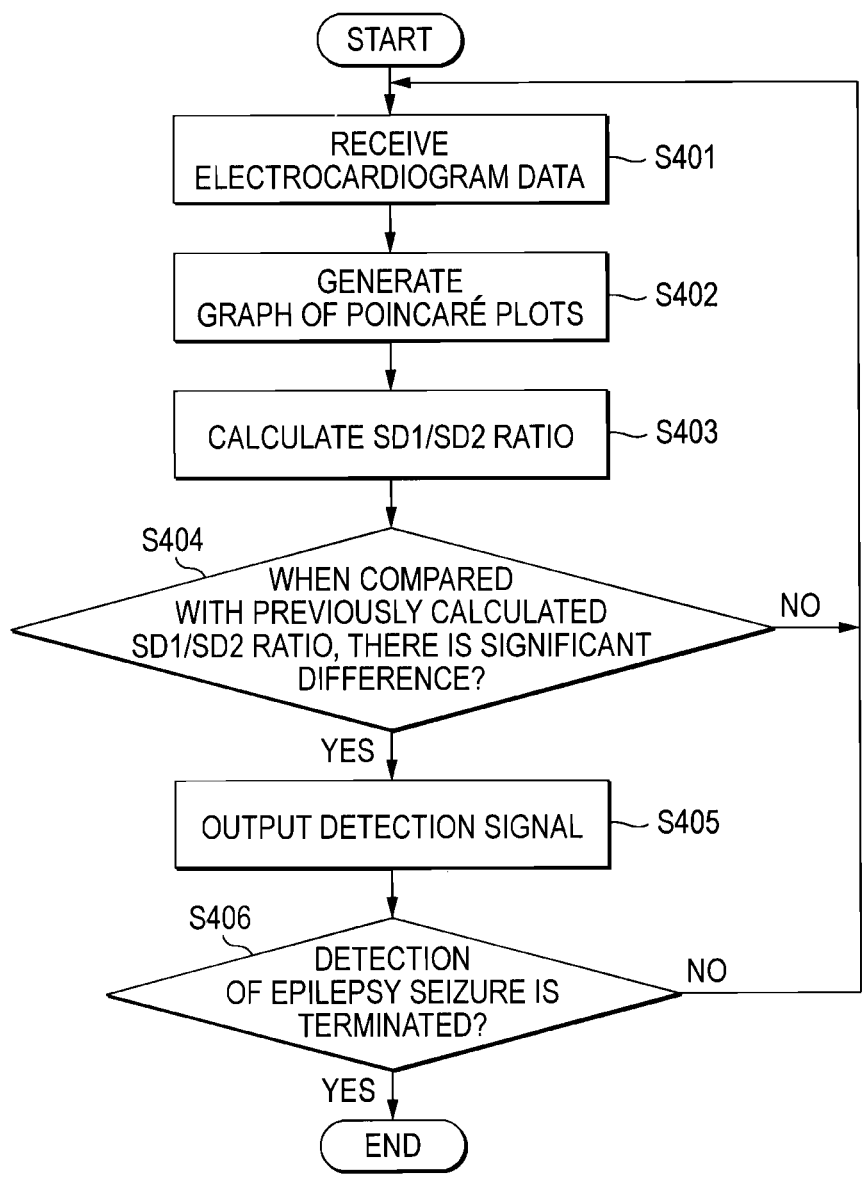
FIG. 4 is a view illustrating a flowchart of a program (method) for detecting an epilepsy seizure according to the embodiment of the invention.

FIG. 4 is a view illustrating a flowchart of a program (method) for detecting an epilepsy seizure according to the embodiment. The program (method) for detecting an epilepsy seizure can be executed by the information processor 200.

The controller 201 receives electrocardiogram data from the biological signal amplifier 100 through the communication interface 204 (S401). The received electrocardiogram data are stored in the data storage 202.

The graph generator 206 generates a graph of Poincaré plots by using the heart beat interval RR which is detected by the heart beat interval detector 205 based on the electrocardiogram data stored in the data storage 202 (S402).

The seizure detector 207 calculates the SD1/SD2 ratio based on Poincaré plots generated by the graph generator 206 (S403). The previously calculated SD1/SD2 ratio is compared with the presently calculated SD1/SD2 ratio, and it is determined whether there is a significant difference or not (S404).

If, in the comparison between the previously calculated SD1/SD2 ratio with the presently calculated SD1/SD2 ratio, it is determined that there is no significant difference, steps S401 to S403 are repeated (S404: NO).

If, in the comparison between the previously calculated SD1/SD2 ratio with the presently calculated SD1/SD2 ratio, it is determined that there is a significant difference, the seizure detector 207 outputs the detection signal through the communication interface 204 (S405).

Steps S401 to S405 are repeated until the user inputs instructions for terminating the detection of an epilepsy seizure (S406).

An epilepsy seizure has a feature that it has unpredictability and recurrence. When a seizure accompanied by impairment of consciousness occurs, therefore, the patient cannot perform a voluntary motion, and hence there is a risk that not only the patient but also another person may cause an accident. Because an epilepsy seizure has the above-described feature, the risk cannot be always reduced unless a seizure can be detected.

When the apparatus for detecting an epilepsy seizure according to the embodiment detects the epilepsy seizure and outputs the detection signal, however, the means for avoiding a danger associated with an epilepsy seizure can be initiated by using the detection signal as a trigger. For example, it is contemplated that the occurrence is informed to the third party, or that, in the case where the subject operates a machine, a function of stopping the machine is activated.

When the apparatus for detecting an epilepsy seizure according to the embodiment detects the epilepsy seizure and outputs the detection signal, the detection signal can be used as a trigger for activating a treatment apparatus for suppressing a seizure. For example, the detection signal for an epilepsy seizure may be used as a trigger for activating a chemical injection pump for suppressing a seizure, or a treatment apparatus such as a brain/neural stimulator.

EXAMPLE

An example of the embodiment will be described.
(Conditions and Method)
(a) Subjects: 19 persons (15 males) of ages 19 to 67.
(b) With respect to 19 epilepsy seizures of refractory temporal lobe epilepsy, the heart beat interval RR was measured by using electrocardiograms generated by an electrocardiograph having a sampling frequency of 200 Hz or 500 Hz. Poincaré plots were generated, and the SD1/SD2 ratios were calculated.
(c) It was considered whether differences of averages of SD1 value, SD2 value, and the SD1/SD2 ratio before and after a seizure are significant or not.

The p-value shown in Table 1 below indicates the probability that, in the case where a null hypothesis that there is no difference in SD1 value, SD2 value, and the SD1/SD2 ratio before and after an occurrence of an epilepsy seizure is generated, measured data are incidentally consistent with the null hypothesis.

(Results)
Table 1 below shows the SD1 value, SD2 value, and SD1/SD2 ratio which were measured in the example, and the p-value.

TABLE 1

|  | Before epilepsy seizure | After epilepsy seizure | p-value |
|---|---|---|---|
| SD1 value [ms] | 33.3 ± 30.2 | 11.0 ± 4.3 | 0.004 |
| SD2 value [ms] | 74.4 ± 49.0 | 117.1 ± 50.6 | 0.012 |
| SD1/SD2 ratio | 0.46 ± 0.27 | 0.11 ± 0.06 | <0.001 |

As shown in Table 1, it has been proven that the difference between the SD1/SD2 ratios before and after an occurrence of an epilepsy seizure is significant, and an epilepsy seizure can be sufficiently detected based on a change of the SD1/SD2 ratio.

In the above, the apparatus and program (method) for detecting an epilepsy seizure according to the embodiment of the invention have been described. The embodiment attains the following effects.

An epilepsy seizure is detected based on a change of the heart beat interval and that of the fluctuation level of the heart beat interval, thereby enabling an epilepsy seizure to be detected without erroneous detection and highly sensitively.

Figure 5:
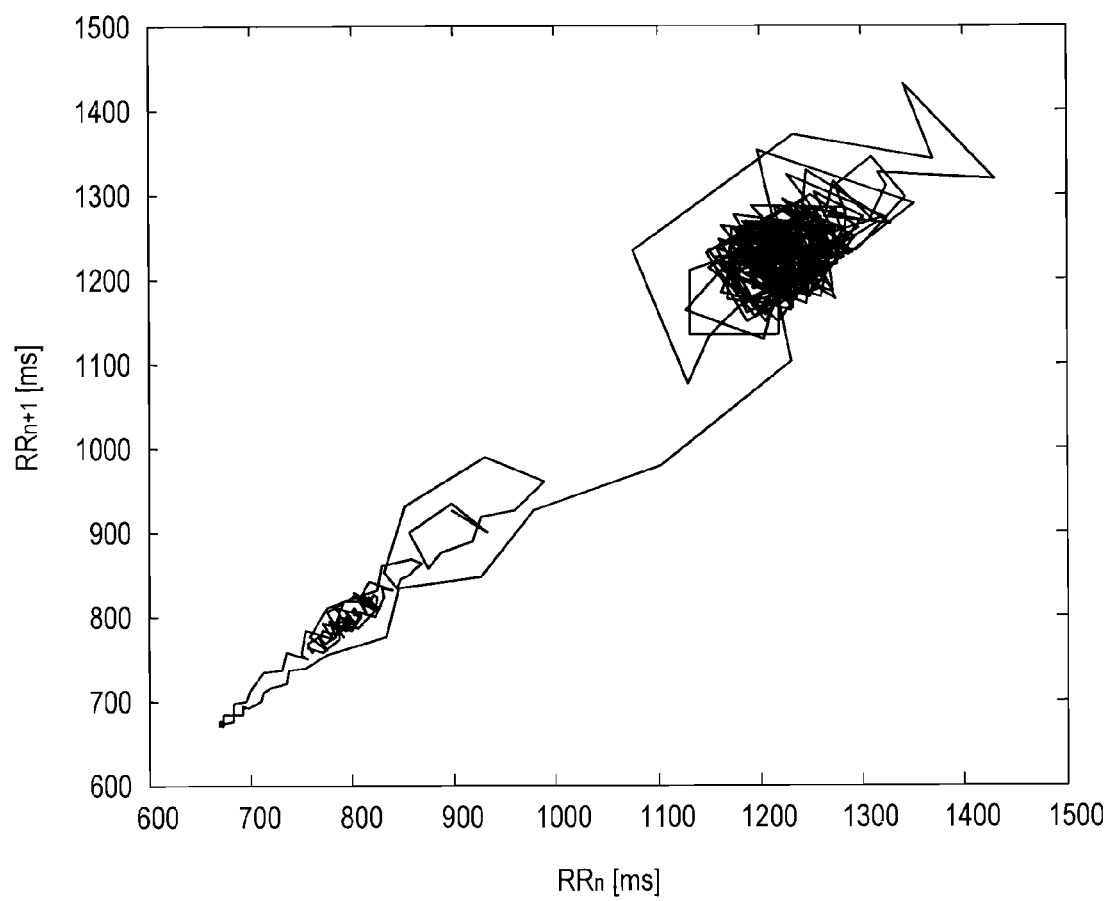
FIG. 5 is a view illustrating a graph in which Poincaré plots are plotted before and after an occurrence of an epilepsy seizure.

As shown in FIG. 5, moreover, a change of the heart beat interval is considered as a movement of a temporal locus of a dot group in Poincaré plots. Next, the fluctuation of the heart beat interval for each heart beat is measured by a change of the distance between the straight line passing the origin and a point where the lateral and vertical coordinates are equal to each other, and a plotted dot. Therefore, an epilepsy seizure can be detected more objectively, without erroneous detection, and highly sensitively. However, the display of a straight-line graph is not an essential condition.

Furthermore, an epilepsy seizure is detected based on a change of the ratio of the standard deviation of the distribution in a graph of Poincaré plots in the direction perpendicular to the straight line passing the origin and a point where the lateral and vertical coordinates are equal to each other, to that of the distribution in the direction parallel to the straight line. Therefore, an epilepsy seizure can be detected with higher reliability.

Furthermore, an epilepsy seizure is detected based on a situation where the ratio of the standard deviation of the distribution in a graph of Poincaré plots in the direction perpendicular to the straight line passing the origin and a point where the lateral and vertical coordinates are equal to each other, to that of the distribution in the direction parallel to the straight line is equal to or smaller than a threshold. Therefore, an epilepsy seizure can be detected with further higher reliability.

When the threshold is set for each subject, furthermore, the sensitivity of detection of an epilepsy seizure can be further improved.

When an epilepsy seizure is detected, the detection signal may be output, so that the detection signal can be used as trigger for stopping a machine which is operated by the patient. Therefore, it is possible to avoid a danger associated with an epilepsy seizure.

The apparatus and program (method) for detecting an epilepsy seizure according to the invention are not limited to the above-described embodiment.

In the embodiment, for example, it has been described that the apparatus for detecting an epilepsy seizure is configured by an information processor and programs which are to be executed by the processor. Alternatively, apart or all of the programs may be replaced with hardware such as a custom LSI (Large Scale Integration).

For example, heart beat intervals in continuous heart beats may be measured, and the heart beat interval at an arbitrary timing and the next heart beat interval may be sequentially plotted on the YZ-, XZ-, or XY-axis of a three-dimensional orthogonal graph.

According to an aspect of the invention, since an epilepsy seizure is detected based on a reduction of the heart beat interval and a change of the fluctuation level of the heart beat interval, an epilepsy seizure can be detected without erroneous detection and highly sensitively.

What is claimed is:
1. An apparatus for detecting an epilepsy seizure, the apparatus comprising:
a graph generating unit configured to generate an orthogonal graph where values of heart beat intervals are sequentially plotted while a heart beat interval at an arbitrary timing is set as a first coordinate and a next heart beat interval is set as a second coordinate; and
a seizure detecting unit configured to detect the epilepsy seizure based on: a change of a distribution of a group of the plotted values in a first direction perpendicular to a straight line passing an origin and a point where the first and second coordinates are equal to each other; and a change of a distribution of the group of the plotted values in a second direction parallel to the straight line,
wherein the seizure detecting unit detects the epilepsy seizure based on: a change of a standard deviation of the distribution in the first direction; and a change of a standard deviation of the distribution in the second direction, and
wherein the seizure detecting unit detects the epilepsy seizure based on a change of a ratio of the standard deviation of the distribution in the first direction to the standard deviation of the distribution in the second direction.
2. The apparatus according to claim 1, wherein the seizure detecting unit detects the epilepsy seizure based on a situation where the ratio is equal to or smaller than a preset threshold.
3. The apparatus according to claim 2, wherein the threshold is set for each subject of the heart beat intervals.

4. The apparatus according to claim 1, further comprising a detection signal outputting unit configured to, when the seizure detecting unit detects the epilepsy seizure, output a detection signal.

5. The apparatus according to claim 1, further comprising a heart beat interval measuring unit configured to measure the heart beat intervals in continuous heart beats, wherein the graph generating unit plots the values of the heart beat intervals which are measured by the heart beat interval measuring unit.

6. The apparatus according to claim 1, wherein the orthogonal graph is a two-dimensional orthogonal graph, the first coordinate is a lateral coordinate, and the second coordinate is a vertical coordinate.

7. A method of detecting an epilepsy seizure, the method comprising:
   generating an orthogonal graph where values of heart beat intervals are sequentially plotted while a heart beat interval at an arbitrary timing is set as a first coordinate and a next heart beat interval is set as a second coordinate; and
   detecting the epilepsy seizure based on: a change of a distribution of a group of the plotted values in a first direction perpendicular to a straight line passing an origin and a point where the first and second coordinates are equal to each other; and a change of a distribution of the group of the plotted values in a second direction parallel to the straight line,
   wherein the epilepsy seizure is detected based on: a change of a standard deviation of the distribution in the first direction; and a change of a standard deviation of the distribution in the second direction, and
   wherein the epilepsy seizure is detected based on a change of a ratio of the standard deviation of the distribution in the first direction to the standard deviation of the distribution in the second direction.

8. The method according to claim 7, wherein the epilepsy seizure is detected based on a situation where the ratio is equal to or smaller than a preset threshold.

9. The method according to claim 8, wherein the threshold is set for each subject of the heart beat intervals.

10. The method according to claim 7, further comprising: outputting a detection signal when the epilepsy seizure is detected.

11. The method according to claim 7, further comprising: measuring the heart beat intervals in continuous heart beats.

12. The method according to claim 7, wherein the orthogonal graph is a two-dimensional orthogonal graph, the first coordinate is a lateral coordinate, and the second coordinate is a vertical coordinate.

13. A non-transitory computer-readable recording medium in which a computer program causing a computer to execute the method according to claim 7 is recorded.

* * * * *